United States Patent [19]

Norris

[11] Patent Number: 5,132,538
[45] Date of Patent: Jul. 21, 1992

[54] MEASURING PERCENTAGE OF PROTEIN IN WHOLE GRAIN SAMPLES

[75] Inventor: Karl Norris, Beltsville, Md.

[73] Assignee: NIRSystems Incorporated, Silver Spring, Md.

[21] Appl. No.: 705,602

[22] Filed: May 24, 1991

[51] Int. Cl.$^5$ .............................. G01N 21/35
[52] U.S. Cl. .................... 250/339; 250/340; 250/341
[58] Field of Search ............ 250/338.1, 339, 340, 250/341

[56] References Cited

U.S. PATENT DOCUMENTS

| | | | |
|---|---|---|---|
| 4,260,262 | 4/1981 | Webster | 356/418 |
| 4,627,008 | 12/1986 | Rosenthal | 250/339 X |
| 4,752,687 | 6/1988 | Satake | 250/339 |
| 4,801,804 | 1/1989 | Rosenthal | 250/341 |
| 4,963,743 | 10/1990 | Satake et al. | 250/339 |
| 4,969,739 | 11/1990 | McGee | 356/308 |
| 4,997,280 | 3/1991 | Norris | 356/308 |

OTHER PUBLICATIONS

"Optimization of Mathematical Treatments of Raw Near-Infrared Signal in the Measurement of Protein in Hard Red Spring-Wheat. I, Influence of Particle Size", Cereal Chemistry, K. H. Norris et al., pp. 158-165, vol. 61, No. 2, 1984.
"Identification of Wavelengths of Near-Infrared Absorbers", Instrumentation Research Laboratory, Near-Infrared Techology in the Agriculture and Food Industries, 1987.

Primary Examiner—Constantine Hannaher
Assistant Examiner—Edward J. Glick
Attorney, Agent, or Firm—Lane, Aitken & McCann

[57] ABSTRACT

In a method for measuring protein content of whole grain kernels with a near infrared spectrophotometer, reflectance measurements are made at wavelengths shorter than 1600 nanometers. The wavelengths are selected to correspond with absorbance bands of the constituents of the sample. The measurements are encoded into absorbance data and are normalized by subtracting the absorbance value at a first wavelength and then dividing the resulting data by the value at a second wavelength. In accordance with one embodiment, the normalized data is substituted in a formula having coefficients determined by regression from samples having known percentages of protein in the sample to yield the percentage of protein in the unknown sample. In accordance with a second embodiment, the second differential of the absorbance data is determined and the resulting differential values are inserted in the formula having coefficients obtained from the known samples to yield the percentage or protein in the unknown sample.

11 Claims, 4 Drawing Sheets

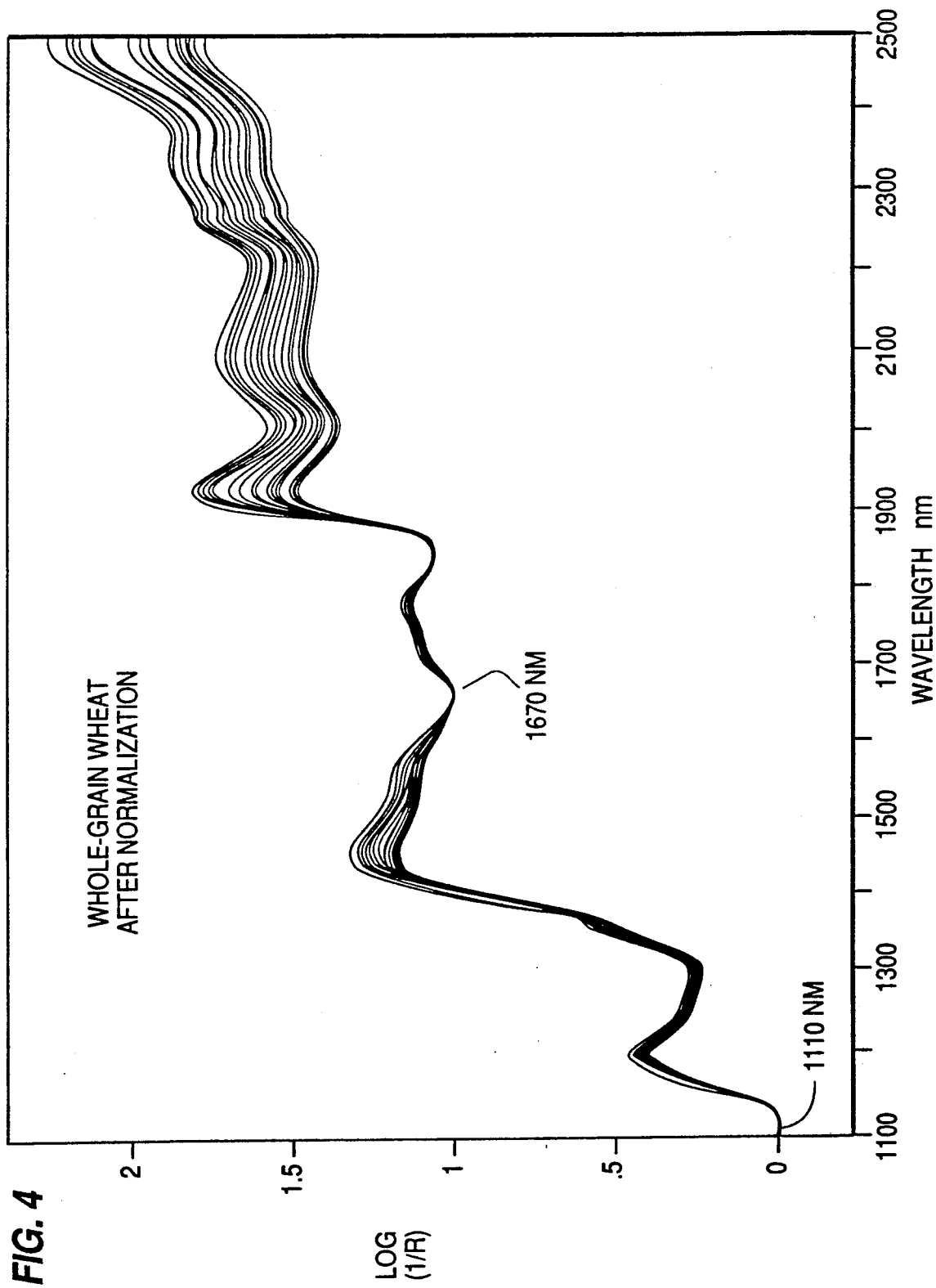

MEASURING PERCENTAGE OF PROTEIN IN WHOLE GRAIN SAMPLES

BACKGROUND OF THE INVENTION

This invention relates to a method for measuring the protein content in grain and, more particularly, to a method of measuring the protein content of whole grain kernels.

The protein content of grain samples as well as the oil and water content of the samples has been measured by systems in the prior art by grinding a sample of the grain to particulate form, irradiating the grain sample with near infrared light, detecting the reflectivity of the sample at narrow band wavelengths in the near infrared spectrum to obtain raw reflectance data. The reflectance data is converted to data representing log 1/R, in which R is the reflectivity. From the log 1/R data, the first or second derivative is determined. The first or second derivative values are inserted into equations in which the coefficients are determined by linear regression on known samples. The resulting values give accurate measurements of the oil, protein and water content of the grain samples, provided the particle size of the particles in the sample are uniform and are sufficiently small.

Prior to the present invention, it has been difficult to obtain accurate measurements of the grain constituents without first grinding the grain.

In prior art methods of measuring grain samples, the reflectance or transmittance of the sample was measured at wavelengths at which relatively strong absorbance by the constituents of the grain sample occurred. The wavelengths selected for measurement were restricted to relatively long near infrared wavelengths in the range of 1600 nanometers to 2500 nanometers. While the grain constituents were known to absorb at shorter near infrared wavelengths, the shorter wavelengths were not used because they yielded results which were less accurate than the measurements at the longer wavelengths. The measurements at the longer wavelengths were quite accurate for ground grain samples.

SUMMARY OF THE INVENTION

The present invention is based on the discovery that highly accurate measurements of the protein content of whole grain samples can be obtained by measuring the samples at shorter near infrared wavelengths, less than 1600 nanometers provided that the reflectance data is properly normalized. The use of the shorter wavelengths, when normalized, yield accurate measurements of whole grain in contrast to the longer wavelength used in the prior art because the shorter wavelengths are less susceptible to nonlinearities caused by surface reflectance from the whole grain kernels.

In accordance with the invention, the reflectance of the whole grain sample is measured at specific near infrared wavelengths, at which protein and other constituents of the grain sample absorb infrared radiation, and at least some of which are under 1600 nanometers. The resulting data is converted into log 1/R data which is then normalized by subtracting the value of the reflectance measurement of the sample at a first wavelength at which the absorbance is low and relatively flat and by dividing each of the measurements by the measurement at a second longer wavelength at which the variation of log 1/R with wavelength is relatively flat. Both the first and second wavelengths used in the normalization process are wavelengths which are short enough to minimize non-linear reflectance effects. The resulting data will then yield a highly accurate measurement of the amount of protein in the sample in accordance with the following equation:

$$\% \text{ protein} = K_0 + K_1 f(R_1) + K_2 f(R_2) + \ldots K_n f(R_n) \tag{1}$$

In this formula, the functions $f(R_1)$ through $f(R_n)$ are functions of the normalized log 1/R data. $K_0$ through $K_n$ are coefficients determined by multiple regression from measurements of grain samples having known percentages of protein. In accordance with one embodiment of the invention, the functions $f(R_1)$ through $f(R_n)$ are the normalized log 1/R data at selected wavelengths all below 1600 nanometers. In accordance with a second embodiment of the invention, the functions $f(R_1)$ through $f(R_n)$ are the second derivatives of the variation of the normalized log 1/R data with wavelength determined at different selected wavelengths. As in the first embodiment the coefficients $K_0$ through $K_n$ are coefficients determined by multiple regression from measurements of grain samples having known percentages of protein. In the embodiment using the second derivative, some of the wavelengths used are greater than 1800 nanometers above which surface effects from the whole grain kernels causes non-linearity, but three wavelengths are below 1800 nanometers and two of those are at absorbance bands for protein. The use of a wavelength in a protein absorbance band below 1600 nanometers is essential in order to obtain an accurate measurement of the percentage of protein in whole grain samples. The wavelengths above 1800 nanometers can be used in the second derivative formula, even though surface reflectance effects causes variations in the output signal from the grain samples because these effects are somewhat mitigated in the second derivative formula by the normalization process and because the measurements at properly selected wavelengths above 1800 nanometers partially compensate for one another.

BRIEF DESCRIPTION OF THE DRAWINGS

FIG. 4 shows the data of FIG. 1 after it has been normalized in accordance with a routine in the program of FIG. 3.

BRIEF DESCRIPTION OF THE PREFERRED EMBODIMENTS

Figure 1:
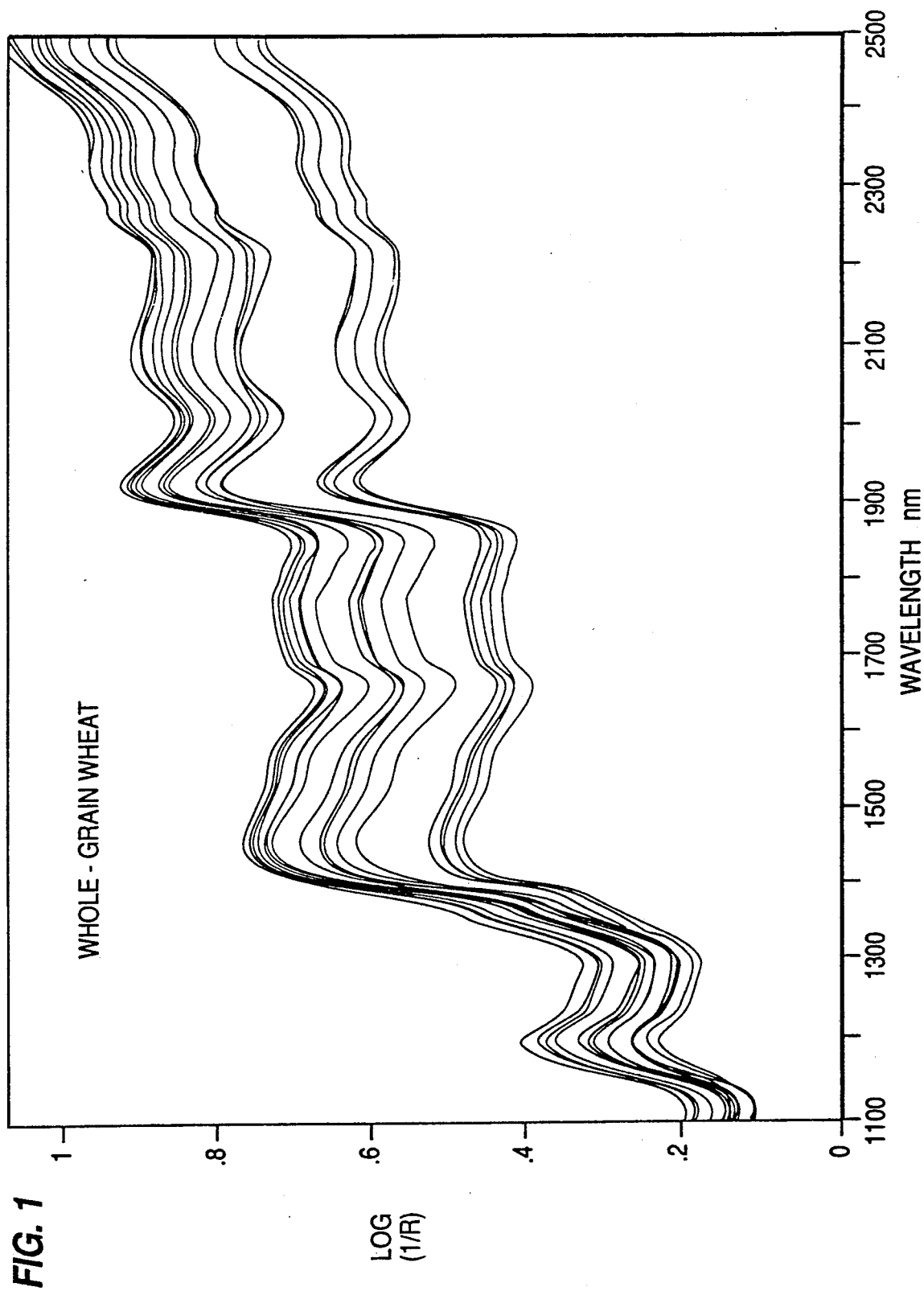
FIG. 1 is a graph illustrating how the absorbance measurements from a plurality of whole grain wheat samples vary with wavelength in the near infrared spectrum.

FIG. 1 is a graph representing the variation in the absorbance, log (1/R) of 16 whole grain wheat samples. As shown in this figure, the absorbance varies considerably from sample to sample. This variation is caused by light scatter from the whole grain kernels and by nonlinear surface reflectance effects. These effects make it difficult to obtain accurate measurements from whole grain samples. The data illustrated in FIG. 1 was obtained from the 16 samples by means of an NIRSystems Model No. 6500, which corresponds to the instrument disclosed in U.S. Pat. No. 4,969,739 to McGee. This instrument may also be used for the method of the present invention.

Figure 2:
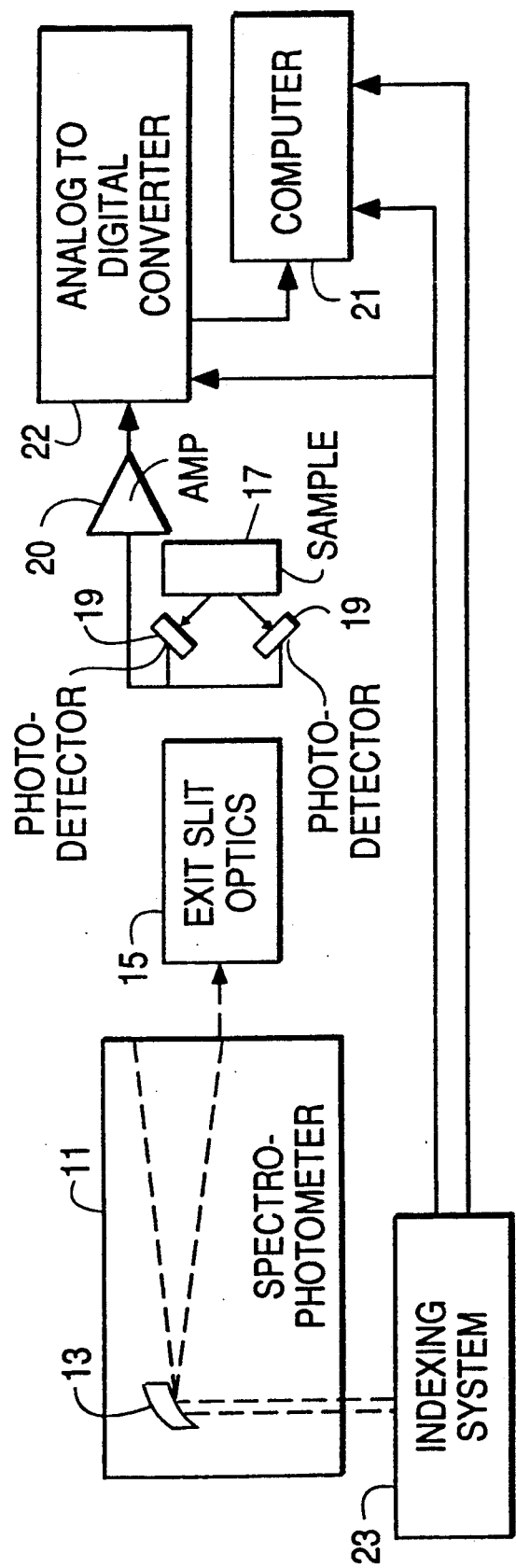
FIG. 2 schematically illustrates an instrument for making the reflectance measurements to determine absorbance values such as illustrated in FIG. 1.

As shown in FIG. 2, the instrument comprises a spectrometer 11 containing an oscillating grating 13. The grating 13 is irradiated with near infrared light and disperses the light into a spectrum. An exit slit in the spectrometer is positioned to transmit a narrow band width of the spectrum dispersed by the grating. As the grating oscillates, the bandwidth of the light passing through the exit slit is scanned through a range of the spectrum dispersed by the grating 13. The light passing through the exit slit is transmitted by exit slit optics 15 to irradiate the sample 17. Light reflected by the sample is detected by photodetectors 19, the output signals of which are combined and applied to an amplifier 20. The amplifier 20 applies an amplified version of the combined photodetector signal to an analog-to-digital converter 22, which converts successive samples of the output signal of the amplifier 20 to digital values. The digital values from the analog-to-digital converter are received by a computer 21. A shaft angle transducer 23 connected with the shaft on which the grating 13 oscillates applies digital signals representing the angular position of the grating in 0.025 degree increments. The analog-to-digital converter 22 applies a digital value to the computer 21 representing the intensity reflected from the sample 17 at each 0.025 degree increment of the grating oscillation.

Each sample is scanned several times and the digital intensity read out at each angular increment is stored. The values obtained at each increment are averaged to obtain an average value at each angular increment. These average values representing the reflected intensity from the sample at each angular increment are converted by simple interpolation to values representing the reflected intensity at two nanometer increments of the center wavelength variation of the narrow bandwidth irradiating the sample 17 as the grating 13 oscillates.

Before each grain sample is measured, a standard sample in the form of a white ceramic tile having high reflectance, which is essentially constant at about 80 percent throughout the 1100 to 2500 nanometer range, is scanned by the instrument to provide standard values at each angular increment. The intensity values from the grain sample and from the standard are converted to logarithms by the computer and the logarithms of the sample values are subtracted from the logarithms of the standard values to obtain measurements corresponding to log 1/R. It is these values which are plotted in the curve shown in FIG. 1. In the specific samples of the invention, the samples measured are whole grain wheat samples. The method of the invention is applicable to other types of whole grain samples, such as soy beans. This technique of obtaining log 1/R data from a grain sample is standard measurement procedure for the NIRSystems Model 6500 instrument.

Figure 3:
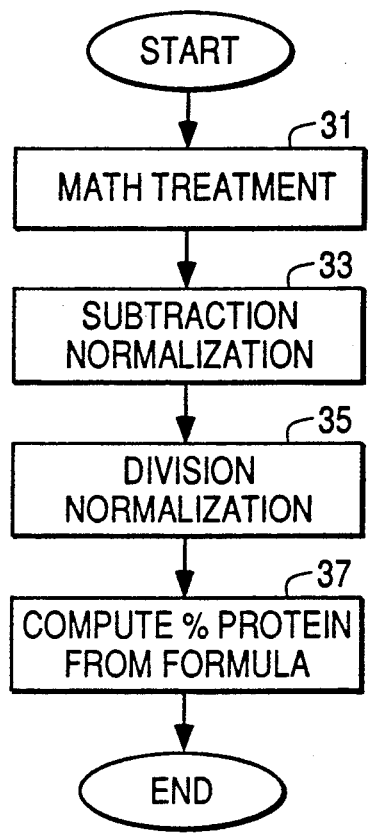
FIG. 3 is a flowchart of a computer program using the system of FIG. 1 to determine the percentage protein in whole grain samples from reflectance values measured by the system shown in FIG. 2.

To obtain accurate measurement values from the whole grain samples, the computer 21 is programmed to carry out the following steps on the log 1/R data obtained from each sample as represented in FIG. 1. The steps carried out by the computer program are illustrated in the flow chart of FIG. 3. As shown in FIG. 3, after a sample has been scanned, the data received by the computer is subjected to math treatment in routine 31. The math treatment is the process described above wherein the average values at each angular increment are determined, the values are converted by interpolation to values at two nanometer increments, the logarithms of the resulting two nanometer increments are determined and subtracted from corresponding logarithms of values obtained from the standard sample. The resulting data, one value for each two nanometer increment from 1100 nanometers to 2500 nanometers will represent a curve such as one of the curves illustrated in FIG. 1. This set of data is then normalized in routine 33 by subtracting from each value in the set, the value in the set determined for the wavelength 1110 nanometers. As pointed out above, the 1110 nanometer wavelength is used for the subtraction normalization step because at 1110 nanometers, the samples have the low absorbance values and the variation in the absorbance values with wavelength is flat. Following the routine 33, the program proceeds into routine 35 in which the division portion of the normalization process is carried out. In this routine, the values obtained for each two nanometer increment in routine 33 are each divided by the value from the set of data obtained in routine 33 at 1670 nanometers. The routine 35 will thus provide a new set of values, one for each two nanometer increment, normalized both by subtraction and division. The value of the data set at 1670 nanometers is chosen for the divisor. Using the value at this wavelength results in a high correlation for protein measurement in whole grain wheat samples by the methods of the invention.

The wavelength used for the subtraction normalization should be shorter than the wavelength used for the division portion and both wavelengths should be where the curves represented by the data are relatively flat, that is where the variation of the log 1/R data with wavelengths is relatively constant. Also, the absorbance value at the wavelength selected for the divisor should differ from the absorbance value at the wavelength selected for the subtraction step to minimize noise effects in the normalized data. In addition, both wavelengths must be sufficiently short that the data is not substantially affected by nonlinearity caused by surface effects from the grain. This means that the wavelength selected from the divisor should be less than 1800 nanometers. Another criteria for the divisor is that it should be chosen so that it avoids strong absorbers in the sample. The data at 1110 and 1670 nanometers for the normalization steps satisfies the above-described considerations to a high degree and achieves excellent correlation in the whole grain measurements. Another wavelength for the divisor which would work substantially as well in the normalization procedure is 1372 nanometers. When the data from the 16 samples has been normalized by the routines 33 and 35, as described above, the resulting data from the 16 samples will appear as shown in FIG. 4. Following the normalization procedure in routine 35, the program enters routine 37 in which the values in the output set of data determined by routine 35 for wavelengths 1128 nanometers, 1154 nanometers, 1188 nanometers, 1200 nanometers, 1212 nanometers, 1218 nanometers, 1254 nanometers and 1320 nanometers are multiplied by coefficients and added together to compute a value of the percentage protein in the sample in accordance with the following formula:

$$\% \text{ protein} = K_0 + K_1 X_{1128} + K_2 X_{1154} + K_3 X_{1188} + \quad (2)$$
$$K_4 X_{1200} + K_5 X_{1212} + K_6 X_{1218} + K_7 X_{1254} + K_8 X_{1320}.$$

wherein the values $X_{1128}$, $X_{1154}$, $X_{1188}$, $X_{1200}$, $X_{1212}$, $X_{1218}$, $X_{1254}$, and $X_{1320}$ are the normalized values of log 1/R obtained in routine 35 at the wavelengths 1128, 1154, 1200, 1212, 1218, 1254 and 1320 nanometers, respectively. In this formula, the absorbance values at 1188 nanometers and 1320 nanometers correspond to protein absorbers in the grain sample. The value at 1154 nanometers is in a moisture band and this term in the equation adjusts the output value for the effect of moisture in the sample. The value at 1200 nanometers is in a starch absorbance band and this term adjusts the output value for the effect of starch contained in the sample. In a similar manner, the value at 1212 nanometers is in an oil absorbance band, the value at 1218 nanometers is in a cellulose absorbance band and these terms adjust the output value obtained from the formula for the amounts of oil and cellulose in the sample. The terms including the values at 1128 nanometers and 1254 nanometers adjust the output value obtained from the formula for unidentified absorbers in grain samples. The coefficients $K_0$ through $K_8$ vary from instrument to instrument and are determined for a given instrument by multiple regression from a series of samples having known amounts of protein. Typical values for these coefficients for NIRSystems Instrument Model No. 6500 are as follows: $K_0 = 4.64$; $K_1 = 2167$; $K_2 = -1355$; $K_3 = 2464$; $K_4 = -759.8$; $K_5 = -6732$; $K_6 = 6881$; $K_7 = -1547$ and $K_8 = 342.5$.

The following table gives an example of the results obtained from 1200 whole grain wheat samples:

TABLE I

| SOURCE | CALIBRATION | | | VALIDATION | | | |
|---|---|---|---|---|---|---|---|
| | SEC | R | NO. | SEP | BIAS | R | NO. |
| 3 YEARS | .238 | .993 | 500 | .233 | .01 | .989 | 1223 |
| 1987 | | | | .231 | .007 | .989 | 473 |
| 1988 | | | | .240 | .02 | .990 | 300 |
| 1989 | | | | .228 | −.01 | .988 | 450 |

The left side of this table shows the calibration data indicating that 500 known samples of whole grain wheat were used to compute the coefficients for formula (2) and that these 500 samples predicted a standard deviation of 0.238 and a correlation coefficient of 0.993. The right side of the table shows the results obtained from 1,223 wheat whole grain samples produced during the years 1987, 1988 and 1989 with the top row of the table indicating the results from all 1,223 samples. The column under SEP indicates the actual standard deviation in the samples as measured, the column under BIAS is the average error, the column under R is the correlation coefficient and the column under NO. is the number of samples. As indicated in Table I, the method and system as described above produces a measurement of the protein content and whole grain samples with a high degree of accuracy.

While the best results are obtained using the specific wavelengths described above, relatively accurate measurements of the percentage protein can be obtained without using all of the wavelengths. For example, the values at just 1188 nanometers and 1320 nanometers for sensing the protein content, the value at 1154 nanometers for sensing the moisture content and the value at 1212 nanometers for sensing the oil content could be used in a four-term formula with reasonably accurate results obtained. In addition, values at different short near infrared wavelengths for measuring the various constituents at which the grain constituents exhibit high absorbance could be used in place of those described above.

Figure 5:
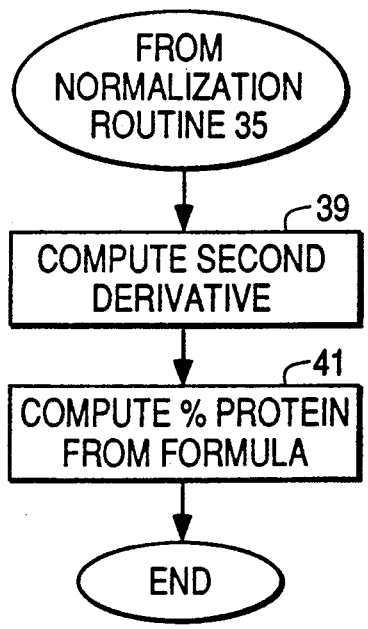
FIG. 5 is a flowchart illustrating an alternative program to be used in the system of FIG. 2 to determine the protein content in whole grain samples from the reflectance data.

In an alternative embodiment, the data is processed in the same manner as described above and illustrated in the flow chart of FIG. 3 except that in the routine 37, a different computation is used to compute the percentage protein. The alternative computation method is illustrated in the flowchart of FIG. 5. As shown in FIG. 5, after the division normalization routine 35 is completed, the program enters routine 39 in which the second derivative of the normalized absorbance data is determined at selected wavelengths. Following routine 39, the program enters into routine 41 in which the percentage of protein is computed from the second derivative set of values determined in routine 39 by inserting the values at selected wavelengths into the following formula:

$$\% \text{ protein} = K_0 + K_1 Y_{1182} + K_2 Y_{1204} + K_3 Y_{1256} + \quad (3)$$
$$K_4 Y_{1982} + K_5 Y_{2266} + K_6 Y_{2318}$$

in which $Y_{1182}$ equals the second derivative of the normalized absorbance value at 1182 nanometers, $Y_{1204}$ equals the second derivative of the normalized absorbance value at 1204 nanometers, $Y_{1256}$ is the second derivative of the normalized absorbance value at 1256 nanometers, $Y_{1982}$ is the second derivative of the normalized absorbance value at 1982 nanometers, $Y_{2266}$ is the second derivative of the normalized absorbance value at 2266 nanometers and $Y_{2318}$ is the second derivative of the normalized absorbance value at 2318 nanometers. As described above, the normalized absorbance values are obtained from the set of data produced in routine 37 and the second derivative values at the selected wavelengths are obtained in routine 39. The coefficients $K_0$ through $K_6$ are obtained by multiple regression from the known samples as described above and vary from instrument to instrument. A typical set of values for the coefficients $K_0$ through $K_6$ in Formula 3 are $K_0 = 1965$; $K_1 = -1596$; $K_2 = 169.2$; $K_3 = 3107$; $K_4 = 198.9$; $K_5 = 152.1$; and $K_6 = 203.0$. In the above formula using the second derivative, the wavelengths at 1182, 1256 and 1982 nanometers in absorbance bands of protein in the grain samples. The remainder of the wavelengths are in absorbance bands of carbohydrates in the grain samples. It will be noted that the second derivative formula uses values obtained at wavelengths greater than 1800 nanometers at which the surface reflectance from the whole grain samples causes variation in the absorbance value measurements. The measurements of these wavelengths can be used in the second derivative formula because the normalization process reduces the surface effects in the second derivative data and the values at which the measurements above 1800 nanometers were made partially compensate for each other. As in the formula using the log 1/R data directly, different wavelengths other than those used in the specific formula can be selected. However, to achieve accurate results from whole grain samples, a plurality of the wavelengths should be below 1600 nanometers and one of the wavelengths below 1600 nanometers must be at an absorbance band for protein in the sample.

Table II illustrates the measurement results by the second derivative method obtained on the same set of samples employed for Table I.

TABLE II

| SOURCE | CALIBRATION | | | VALIDATION | | | |
|---|---|---|---|---|---|---|---|
| | SEC | R | NO. | SEP | BIAS | R | NO. |
| 3 YEARS | .218 | .994 | 500 | .225 | .01 | .990 | 1223 |
| 1987 | | | | .225 | .03 | .990 | 473 |
| 1988 | | | | .219 | −.01 | .993 | 300 |
| 1989 | | | | .227 | −.002 | .988 | 450 |

As indicated in Table 2, the second derivative method provides an equally accurate method of measuring whole grain samples.

The above description is of a preferred embodiment of the invention and modification may be made thereto without departing from the spirit and scope of the invention, which is defined in the appended claims.

I claim:

1. A method of determining the percentage of protein in a whole grain sample, comprising determining a first set of values varying with the absorbance of said sample at a multiplicity of near infrared wavelengths, a plurality of said wavelengths being less than 1600 nanometers, normalizing said first set of values by first subtracting from each of said first set of values one of said first set of values to determine a second set of values, and then dividing each of said second set of values by one of the values of said second set to determine a set of normalized values, and determining the percentage of protein in said sample from the formula: $K_0 + K_1 f(R_1) + K_2 f(R_2) + \ldots K_n f(R_n)$, wherein $f(R_1)$ through $f(R_n)$ are values related to said set of normalized values, at least one of said values of $f(R_1)$ through $f(R_n)$ being related to one of said normalized values at a wavelength less than 1600 nanometers in an absorbance band of protein in said sample, and wherein $K_0$ through $K_n$ are coefficients determined by multiple regression from a multiplicity of samples of grain, each of said multiplicity of samples containing a known amount of protein.

2. A method of determining the percent of protein in a sample as recited in claim 1, wherein said values $f(R_1)$ through $f(R_n)$ are said set of normalized values and each of said values of $f(R_1)$ and $f(R_n)$ are at wavelengths less than 1600 nanometers.

3. A method as recited in claim 1, wherein said values of $f(R_1)$ through $f(R_n)$ are the second derivatives of the variation of said normalized values with wavelength.

4. A method of measuring percent protein in a whole grain sample as recited in claim 1, wherein a plurality of said values of $f(R_1)$ through $f(R_n)$ are at wavelengths in the absorbance bands of constituents in said sample.

5. A method of measuring protein in a sample as recited in claim 4, wherein one of said constituents is carbohydrate.

6. A method as recited in claim 4, wherein two of said constituents are oil and water.

7. A method as recited in claim 1, wherein said values of $f(R_1)$ through $f(R_n)$ comprise said set of normalized values at 1128 nanometers, 1154 nanometers, 1188 nanometers, 1200 nanometers, 1212 nanometers, 1218 nanometers, 1254 nanometers and 1320 nanometers.

8. A method of determining percent protein as recited in claim 1, wherein said values of $f(R_1)$ through $f(R_n)$ comprise the second derivatives of the variation of said set of normalized values at 1182 nanometers, 1204 nanometers 1256 nanometers, 1982 nanometers, 2266 nanometers, and 2318 nanometers.

9. A method as recited in claim 1, wherein said one of said first values is at 1110 nanometers and said one of said second set of values is at 1670 nanometers.

10. A method as recited in claim 1, wherein said one of said first values is at 1110 nanometers and said one of said second values is at 1372 nanometers.

11. A method as recited in claim 1, wherein said first set of values are log 1/R values in which R is the reflectivity of the sample.

* * * * *